US006699999B2

United States Patent

(12) United States Patent
Takahashi et al.
(10) Patent No.: US 6,699,999 B2
(45) Date of Patent: Mar. 2, 2004

(54) PROCESS FOR PRODUCING PYROMELLITIC ANHYDRIDE

(75) Inventors: Tsukasa Takahashi, Himeji (JP); Hiroyuki Uhara, Tatsuno (JP); Kazuo Anyouji, Himeji (JP); Etsushige Matsunami, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 57 days.

(21) Appl. No.: 10/213,083

(22) Filed: Aug. 7, 2002

(65) Prior Publication Data

US 2003/0032816 A1 Feb. 13, 2003

(30) Foreign Application Priority Data

Aug. 8, 2001 (JP) ...................................... 2001-241035

(51) Int. Cl.[7] ............................................ C07D 493/02
(52) U.S. Cl. ..................................................... 549/239
(58) Field of Search ......................................... 549/239

(56) References Cited

U.S. PATENT DOCUMENTS

| | | | | |
|---|---|---|---|---|
| 4,665,200 A | * | 5/1987 | Nakanishi et al. | 549/239 |
| 5,387,699 A | * | 2/1995 | Wagner et al. | 549/239 |
| 6,084,109 A | * | 7/2000 | Chu et al. | 549/239 |
| 6,153,767 A | * | 11/2000 | Sagane et al. | 549/239 |
| 6,433,190 B1 | * | 8/2002 | Yoon et al. | 549/239 |

FOREIGN PATENT DOCUMENTS

| | | | |
|---|---|---|---|
| BE | 655686 | | 1/1965 |
| JP | 44-29446 | | 12/1969 |
| JP | 45-4978 | | 2/1970 |
| JP | 45-15018 | | 5/1970 |
| JP | 45-15252 | | 5/1970 |
| JP | 47-38431 | | 9/1972 |
| JP | 48-35251 | | 10/1973 |
| JP | 49-9451 | | 3/1974 |
| JP | 49-30821 | | 8/1974 |
| JP | 49-31973 | | 8/1974 |
| JP | 56-8388 | A | 1/1981 |
| JP | 57-38745 | A | 3/1982 |
| JP | 61-25642 | A | 2/1986 |
| JP | 61-27942 | A | 2/1986 |
| JP | 63-7537 | B2 | 2/1988 |
| JP | 1-245857 | A | 10/1989 |
| JP | 1-294679 | A | 11/1989 |
| JP | 4-13026 | B2 | 3/1992 |
| JP | 4-15020 | B2 | 3/1992 |
| JP | 8-41067 | A | 2/1996 |
| JP | 11-104497 | A | 4/1999 |
| JP | 2000-79344 | A | 3/2000 |

* cited by examiner

*Primary Examiner*—Deborah Lambkin
(74) *Attorney, Agent, or Firm*—Sughrue Mion, PLLC

(57) ABSTRACT

The present invention has for its object to provide a production method of a pyromellitic anhydride which is not only conducive to an increased catalyst life and, hence, an enhanced operating rate of a plant (reduced downtime) and a reduction in catalyst cost but also conducive to reductions in byproducts and, hence, savings in the cost of after-treatments such as collection and purification.

A production method of a pyromellitic anhydride comprising a step for catalytic gas-phase oxidation of a starting mixture gas consisting of a tetraalkylbenzene and/or a trialkylbenzaldehyde and a molecular oxygen-containing gas in a fixed-bed type reactor having a catalyst bed wherein the production method of a pyromellitic anhydride is carried out under the condition that the moisture content of said starting mixture gas to be introduced into the catalyst bed is not more than 2 volume %.

2 Claims, 1 Drawing Sheet

PROCESS FOR PRODUCING PYROMELLITIC ANHYDRIDE

FIELD OF THE INVENTION

The present invention relates to a process for producing pyromellitic anhydride from a tetraalkylbenzene and/or a trialkylbenzaldehyde by the catalytic gas-phase oxidation method.

BACKGROUND OF THE INVENTION

Pyromellitic anhydride is a compound of value as various industrial starting materials, finding application in heat-resistant resins, plasticizers, curing agents for epoxy resin, and so on. For the production method of pyromellitic anhydride, several processes have heretofore been proposed, and for the catalytic gas-phase oxidation of 1,2,4,5-tetraalkylbenzenes, for instance, relevant technologies are disclosed in Japanese Kokoku Publication Sho-49-9451 and Japanese Kokoku Publication Hei-4-15020, among others. Furthermore, the process for liquid-phase oxidation of 1,2,4,5-tetraalkylbenzenes (Japanese Kokai Publication Sho-61-27942), the process for liquid-phase oxidation of 2,4,5-trimethylbenzaldehyde (Japanese Kokai Publication Sho-57-38745), and the catalytic gas-phase oxidation process starting with anthracene (Japanese Kokai Publication Sho-56-8388) have also been disclosed.

Regarding the catalyst for the production of pyromellitic anhydride by the catalytic gas-phase oxidation, the following catalysts, among others, have been disclosed: $V_2O$—TiO2, $WO_2$ type (Belgian Patent 655686), $V_2O_5$—$P_2O_5$—$TiO_2$, $MoO_3$, $WO_3$(Japanese Kokoku Publication Sho-45-4978), $V_2O_5$—$TiO_2$(anatase-type) —$MoO_3$, $P_2O_5$(Japanese Kokoku Publication Sho-45-15018), $V_2O_5$—$TiO_2$—$Na_2O$—$P_2O_5$ type (Japanese Kokoku Publication Sho-45-15252), $V_2O_5$—$MoO_3$—$P_2O_5$ (Japanese Kokoku Publication Sho-47-38431), $V_2O_5$—$TiO_2$—$P_2O_5$—$Nb_2O_5$—$K_2O$, $P_2O_5$, $TiO_2$, $Na_2O$ (Japanese Kokoku Publication Sho-49-31973), $V_2O_5$—$B_2O_5$ (Japanese Kokoku Publication Sho-48-35251), $V_2O_5$—$Na_2O$—$MoO_3$—Cr, Mn, Nb (Japanese Kokai Publication Hei-1-294679), $V_2O_5$—$WO_3$—$TiO_2$ (rutile-type) —Mn, Sb, Te, Bi, P, Cu, Al, Group VIIIB, alkali metal (Japanese Kokai 2000-79344).

Furthermore, referring to the mode of use of the catalyst for the production of pyromellitic anhydride, particularly to examples in which the catalyst bed is divided into two or more stages, Japanese Kokoku Publication Hei-4-15020, Japanese Kokai Publication Hei-1-245857 and Japanese Kokoku Publication Hei-4-13026, for instance, disclose technologies for suppressing the reaction in the hot spot of a catalyst bed to thereby reduce the temperature of said hot spot, which comprise either diluting the catalyst with a carrier, increasing the catalyst diameter, reducing the supported amount of the catalyst, adjusting the vanadium, alkali metal or phosphorus content of the catalyst, or reducing the specific surface area of $ZrO_2$, $TiO_2$ or $SnO_2$. Japanese Kokai Publication Hei-8-41067 discloses the method comprising using a Mo-supplemented catalyst for the catalyst bed on the reaction gas outlet side, or a catalyst supplemented with a large amount of an alkali metal for the catalyst bed on the reaction gas inlet side to improve the yield of pyromellitic anhydride.

Furthermore, as the reaction technology for the production of pyromellitic anhydride, Japanese Kokoku Publication Sho-63-7537 discloses a method of increasing the product yield which comprises adding water vapor to the reactant gas to be introduced into the catalyst bed.

Although pyromellitic anhydride can be produced by such various alternative techniques as mentioned above, it was insufficient concerning the study regarding the catalyst life. In Japanese Kokoku Publication Sho-44-29446it is stated that a 30-hour intermittent reaction entailed a yield reduction of 1.9 weight %. According to Japanese Kokai Publication Sho-61-25642, a one-month-long operation under low-oxygen concentration, high moisture content, high reaction temperature conditions resulted in a yield reduction of 0.9 mole %, and Japanese Kokai Publication Hei-11-104497 states that a 3-month-long operation resulted in a yield reduction of 0.2 mole %, 2.5 mole %. To cope with the above problem, Japanese Kokoku Publication Sho-45-4978 teaches a combination of V with P, Ti, W and Mo as a means for improving the aging of vanadium oxide type catalysts and states that this measure proved effective in a 30-hour intermittent operation. Japanese Kokoku Publication Sho-49-30821 referring to a supported V—P—Mo catalyst as immobilized on a molten alumina carrier, discloses that addition of Ti suppressed the yield loss to 0.5 mole % in a 1500-hour operation. However, even these techniques are inadequate in the effect of suppressing catalyst aging and have room for further improvement in the curtailment of the interval between catalyst changes. Thus, in commercial production, catalyst change is a significant factor leading to increased production cost owing to downtime and gain in catalyst cost so that a further improvement in catalyst life is required.

Meanwhile, in the production of pyromellitic anhydride, it was known until recently that the water vapor content of the starting material gas influences the reaction to enhance the yield of pyromellitic anhydride (PMDA) in the early stage of reaction (Japanese Kokoku Publication Sho-63-7537). However, there is no report on the effect which the water vapor content of the starting material gas may have on the time-dependent change of yield.

SUMMARY OF THE INVENTION

Developed in the above state of the art, the present invention has for its object to provide a production method of a pyromellitic anhydride which is not only conducive to an increased catalyst life and, hence, an enhanced operating rate of a plant (reduced downtime) and a reduction in catalyst cost but also conducive to reductions in byproducts and, hence, savings in the cost of after-treatments such as collection and purification.

The inventors of the present invention took note of the fact that change of the fixed-bed catalyst in the fixed-bed type reactor is so costly and time-consuming that the influence of catalyst life on economics is remarkable and further that in the case where the aging of the catalyst is severe, operating parameters must also be modified frequently with the result that even the operation itself may become difficult. Accordingly, we dared to explore into the aging behavior of the catalyst at a low water vapor concentration which is usually a cause for poor initial yield and found that the water vapor concentration exerts a profound influence on catalyst aging. As a result, we established a technology promising a high yield when the catalyst is used for at least 2000 hours and a still greater advantage when the operation is further prolonged. Thus, the inventors paid attention to the reaction parameters for a production method of a pyromellitic anhydride comprising a step for catalytic gas-phase oxidation of a starting mixture gas consisting of a tetraalkylbenzene and/or a trialkylbenzaldehyde and a molecular oxygen-containing gas in a fixed-bed type reactor having a catalyst bed and investigated them with great care and, as a result, found that the moisture content (the water vapor content) of the starting mixture gas to be introduced into the catalyst bed has a significant effect on catalyst aging and have succeeded in prolonging the catalyst life by reducing said content of water vapor to a certain level or below. We discovered, at the same time, that, by reducing the content of water vapor to such a low level, the formation of byproducts can also be suppressed to neatly resolve the above-mentioned problems. The present invention has been developed on the basis of the above findings.

The present invention, therefore, is concerned with a production method of a pyromellitic anhydride comprising a step for catalytic gas-phase oxidation of a starting mixture gas consisting of a tetraalkylbenzene and/or a trialkylbenzaldehyde and a molecular oxygen-containing gas in a fixed-bed type reactor having a catalyst bed wherein the production method of a pyromellitic anhydride is carried out under the condition that the moisture content of said starting mixture gas to be introduced into the catalyst bed is not more than 2 volume %.

The present invention further relates to a production method of a pyromellitic anhydride comprising a step for catalytic gas-phase oxidation of a starting mixture gas consisting of a tetraalkylbenzene and/or a trialkylbenzaldehyde and a molecular oxygen-containing gas in a fixed-bed type reactor having a catalyst bed wherein the production method of a pyromellitic anhydride is carried out by dehumidifying the molecular oxygen-containing gas.

DETAILED DESCRIPTION OF THE INVENTION

Figure 1:
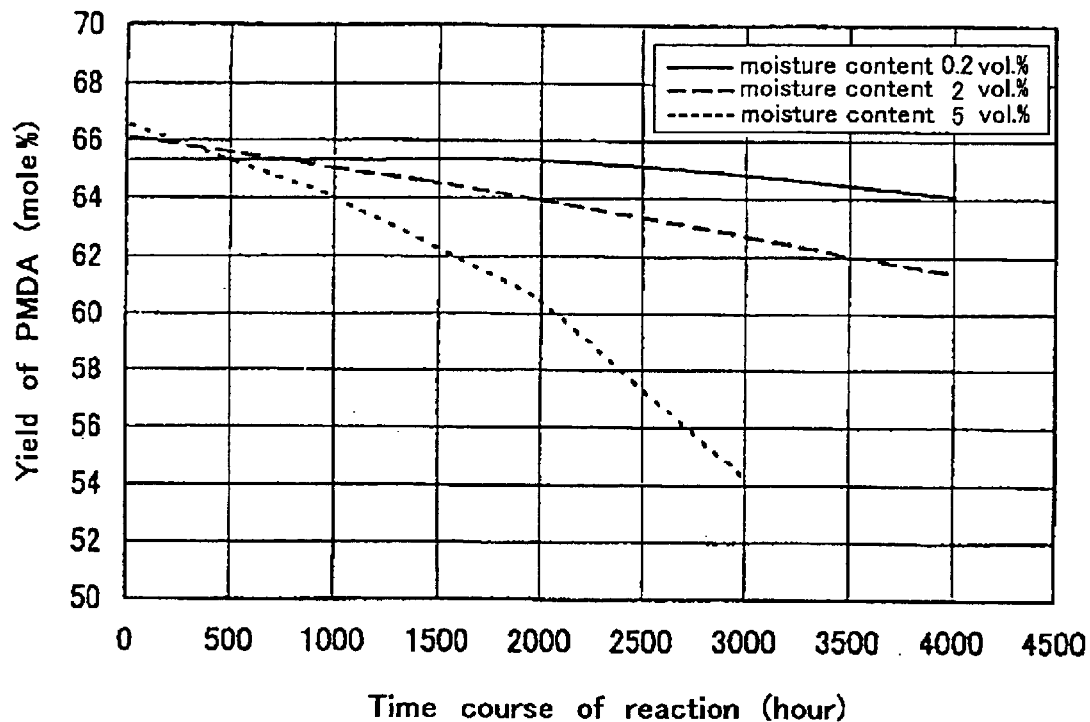
FIG. 1 is a diagrammatic representation of the relationship of the time course of reaction to the yield of PMDA in Examples and Comparative Example.

In the following, the present invention is now described in detail.

The production method of the present invention comprises a catalytic gas-phase oxidation step in which (1) either the moisture content of the starting mixture gas to be introduced into the catalyst bed is controlled at a maximum of 2 volume % (vol. %) or (2) the molecular oxygen-containing gas is dehumidified. It should, however, be noted that the control according to (1) is preferably effected by the dehumidification according to (2). Thus, a preferred method of reducing the moisture content (concentration of water vapor) of the starting mixture gas to not more than 2 volume % is to reduce the moisture content of the molecular oxygen-containing gas which accounts for more than half the starting mixture gas. When air is used as said molecular oxygen-containing gas, a locality where the atmospheric air is lean in moisture can be properly chosen as the location of the plant but otherwise the molecular oxygen-containing gas should be dehumidified. The method for removing water vapor is not particularly restricted but includes the method comprising reducing the saturation water vapor concentration with a refrigerating machine and removing the condensate water, the method utilizing a compressor, the method using an adsorbent, and a method using them in combination, among others. While, in the preferred embodiment of the present invention, the molecular oxygen-containing gas is dehumidified to bring the moisture content of the starting mixture gas to be introduced into the catalyst bed to 2 volume % or less, it holds substantially true that when the moisture content of the molecular oxygen-containing gas is reduced to 2 volume % or less, the moisture content of the starting mixture gas is also reduced to 2 volume % or less. Preferably, the moisture content of the starting mixture gas or the molecular oxygen-containing gas is reduced to 1.5 volume % or less. More preferably, the moisture content is reduced to 1.0 volume % or less.

The beneficial effects of the present invention are that (1) the rate of deterioration of catalyst is reduced and that (2) the amount of impurity (byproducts other than $CO_2$ and CO), among others, is reduced. Referring to the first-mentioned effect (1), it can be pointed out when the moisture content is not higher than 2 volume %, an average yield of as high as about 64 mole % can be maintained by changing the catalyst with a frequency of not more than twice a year so that both the material cost and catalyst cost can be economized. However, when the moisture content is high, the frequency of catalyst change must be increased in order that the material cost may be suppressed by a comparable degree, with the result that the catalyst cost is increased. Conversely, if the reaction is continued for 4,000 hours or longer in disregard of reductions in the yield, the material cost will be increased inevitably, with the result that the cost of production of pyromellitic anhydride is increased. Referring to the above effect (2), the curtailment in the amount of impurity results in improved product quality and reduced costs of collection and purification.

In this connection, the time courses of PMDA yield were studied in cases where molecular oxygen-containing gases with water vapor concentrations of 5 volume %, 2 volume % and 0.2 volume %, respectively, were used. The results are shown in the Example, Comparative Example, and FIG. 1. The average yields up to various points of time at 1,000-hour intervals as calculated by integration of trapezoid areas are shown in FIG. 2.

Figure 2:
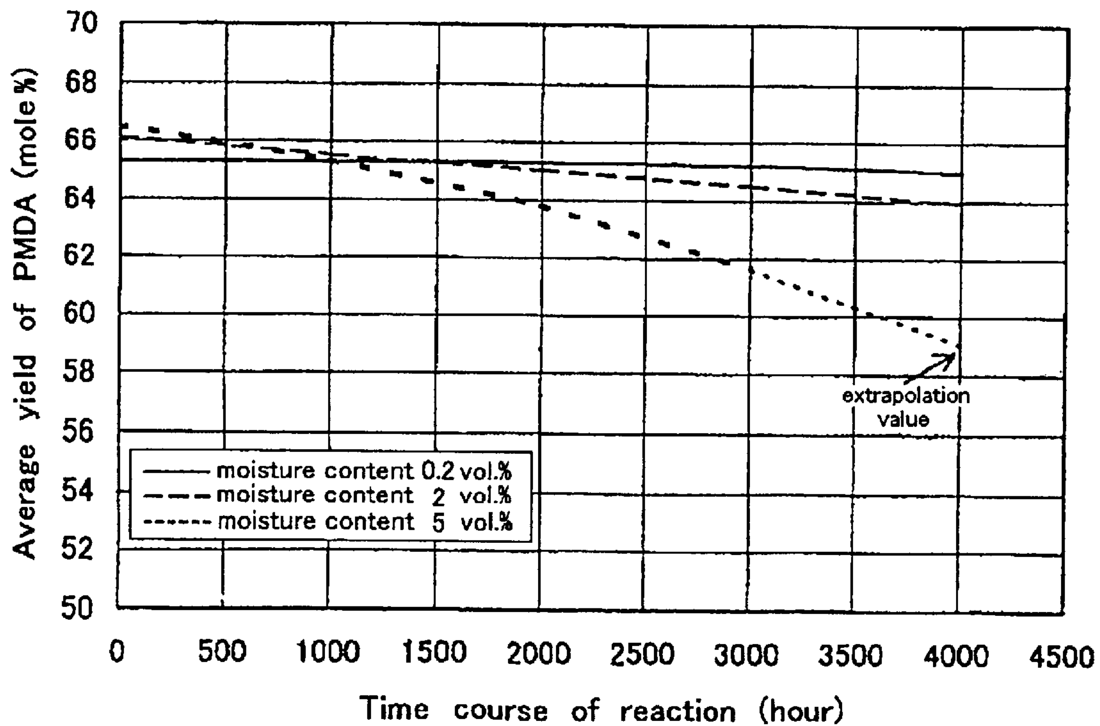
FIG. 2 is a diagrammatic representation of the relationship of the time course of reaction to the average yield of PMDA in Examples and Comparative Example.

As shown in FIG. 1, when a molecular oxygen-containing gas with a water vapor concentration of 5 volume % was used, the initial yield was high but the reduction in yield with time course was remarkable as compared with the case in which molecular oxygen-containing gases with water vapor concentrations of 2 volume % and 0.2 volume % were used. Further, after about 500 hours of operation, the yield was rather higher in the cases where molecular oxygen-containing gases with water vapor concentrations of 2 volume % and 0.2 volume % were used. Then, as shown in FIG. 2, the average yield became almost comparable at 1,000 hours under all the conditions. Furthermore, after 2,000 hours, whereas the average yields in cases where molecular oxygen-containing gases with water vapor contents of 0.2 volume % and 2 volume % were used were approximately 65 mole %, the average yield in the case where a molecular oxygen-containing gas with a water vapor content of 5 volume % was used was about 64 mole %. Thus, a difference of 1 mole % in average yield occurred, so that the cases where molecular oxygen-containing gas with the moisture content of 2 volume % or less were used become advantageous. As can be seen in FIG. 2, this difference became more pronounced as the use of the catalyst was prolonged and was as large as about 3 mole % at 3,000 hours. At 4,000 hours, whereas the yield was about 64 mole % in the case of 2 volume % water vapor or about 65 mole % in the case of 0.2 volume % water vapor, the yield in the case of 5 volume % water vapor was about 59 mole % or less, though it was an estimate by extrapolation. Thus, a marked difference of about 5 mole % could be obtained by controlling the water vapor concentration of the molecular oxygen-containing gas at 2 volume % or less.

In addition, the practice of reducing the water vapor content of the starting mixture gas has an additional advantage that the formation of byproducts is suppressed as can be seen from the following example. Thus, the production amount of trimellitic acid is 4.5 mole % in the case where air containing 5 volume % of water vapor was used as the molecular oxygen-containing gas, 3.5 mole % in the case where air containing 2 volume % of water vapor was used, or 2.8 mole % when air containing 0.2 volume % of water vapor was used. In accordance with the present invention, therefore, the product quality can be improved and the recovery rate in the trapping and purification stage can also be enhanced.

The starting mixture gas to be used in the above catalytic gas-phase oxidation step is composed of a tetraalkylbenzene and/or a trialkylbenzaldehyde and a molecular oxygen-containing gas as mentioned above and optionally may contain other components additionally. The preferred starting mixture gas is one predominantly composed of said tetraalkylbenzene and/or trialkylbenzaldehyde and said molecular oxygen-containing gas.

The species of said tetraalkylbenzene and/or trialkylbenzaldehyde for use in said starting mixture gas may be used each independently or in a combination of two or more different species. Furthermore, compounds having an alkyl group of any arbitrary kind can be used. However, the larger the number of carbon atoms of the alkyl group is, the greater the amount of heat generated in the oxidation reaction is. Therefore, the number of carbon atoms of the alkyl group is preferably as few as possible. Thus, a compound having alkyl groups of 1 to 3 carbon atoms can be used with advantage. For the low-cost production of pyromellitic anhydride, 1,2,4,5-tetramethylbenzene and/or 2,4,5-trimethylbenzaldehyde are particularly preferred, for these starting compounds are conducive to higher product yields. The reaction may optionally be carried out using a mixture of a 2,4,5-trialkylbenzaldehyde and a 1,2,4,5-tetraalkylbenzene, wherein the blending ratio is not restricted.

Referring to the catalyst bed in the fixed-bed type reactor which is used in said catalytic gas-phase oxidation step, the form of the catalyst is not particularly restricted but may be whichever of a supported catalyst and a molded catalyst. The supported catalyst means a catalyst obtained by coating an inert carrier with a catalytic active component and, any of the known coating techniques such as spray coating method, dipping method, rotary granulation method, and so forth, can be utilized. The molded catalyst is a catalyst obtained by molding a catalytic active component and, any of the known molding techniques such as extrusion method and compression molding method and so forth can be utilized. The catalytic active component of such a catalyst means a substance having catalytic activity in the composition of a catalyst and the substance which does not satisfy this definition can be mentioned as the carrier of a supported catalyst. A molded catalyst, except in special cases, may be regarded as a catalyst consisting solely by the active substance. As for special cases, an inert inorganic powder is added as a diluent to suppress the catalytic activity.

The catalyst mentioned above is preferably a catalyst containing vanadium as the catalytic active component, more preferably additionally containing at least one element selected from the group consisting of molybdenum, tungsten, phosphorus, boron, silver, antimony, sulfur, niobium, alkaline earth metal, and rare earth elements. These elements are preferably used within the range not over 3, more preferably, not over 2 atomic ratio of such other elements based on vanadium.

The above catalyst may be optionally supplemented with at least one inorganic oxide selected from titanium oxide, zirconium oxide and tin oxide. By adding any of them in an appropriate amount, it becomes possible to improve the yield of pyromellitic anhydride and the heat resistance of the catalyst. Thus, more preferably said catalytic active component additionally contains at least one inorganic oxide powder selected from the group consisting of $TiO_2$, $ZrO_2$ and $SnO_2$. The preferred level of use of such inorganic oxide may for example be such that, based on the total sum of the number of moles of the above catalyst component elements, the surface area of the inorganic oxide powder so added will be more than 0 but not more than $1\times10^5$ $m^2$/mole, more preferably $1\times10^2$ to $1\times10^5$ $m^2$/mole, most preferably $1\times10^2$ to $4\times10^4$ $m^2$/mole.

The surface area ($m^2$/mole) of the inorganic oxide powder to be added is the value found by multiplying the mass (g) of the used oxide powder by the specific surface area ($m^2$/g) of said oxide and dividing the product by the total sum of moles of used element as metal. The specific surface area mentioned above is the area measured by the BET (Brunaer-Emmett-Teller) method.

The preparation method and the raw materials for such catalysts are not particularly restricted but the conventional techniques and materials can be utilized. Referring to the raw materials, the inorganic salts, such as nitrates, sulfates, hydrochlorides, phosphates, carbonates, etc., the organic acid salts, such as oxalates, citrates, tartrates, etc., the complex salts, or the oxides of the elements to be used can be employed. By the calcinating operation for catalyst preparation, these are thought to become the corresponding oxides or complex oxides in the catalyst. As to titanium oxide, zirconium oxide and tin oxide, commercial oxide powders or oxide powders prepared from the corresponding salts can be employed and those having BET specific surface areas in the range of 5 to 100 $m^2$/g can be used preferably.

The reaction in said catalytic gas-phase oxidation step is preferably carried out in a fixed-bed type reactor packed with the catalyst and passing said starting mixture gas composed of either a 1,2,4,5-tetraalkylbenzene or a 2,4,5-trialkylbenzaldehyde, or a mixture of a 1,2,4,5-tetraalkylbenzene and a 2,4,5-trialkylbenzaldehyde, and a molecular oxygen-containing gas through the catalyst bed in the tubular reactor held in a heat medium controlled at a predetermined temperature. For industrial production, a heat-exchange type multi-tubular reactor, which is commonly used for gas-phase oxidation reaction, comprising a plurality of tubular reactors sharing in the feed gas inlet space and outlet space and held in a heat medium can be used with advantage. The diameter of the tubular reactor is not particularly restricted but tubes having inside diameters in the range of 15 mm to 30 mm, which are used for catalytic gas-phase oxidation reactions in general, can be employed.

In said catalytic gas-phase oxidation step, the reaction conditions are not particularly restricted but the space velocity is preferably 500 to 10000 $h^{-1}$, particularly 1000 to 8000 $h^{-1}$. The reaction temperature is 300 to 500° C., preferably 350 to 450° C., in terms of the temperature of the heat medium. The concentration of the starting mixture gas in mass per $m^3$ of the molecular oxygen-containing gas ($g/m^3$, standard condition) is 10 to 100 $g/m^3$, preferably 10 to 50 $g/m^3$. The molecular oxygen-containing gas may be air, oxygen or a mixture gas composed of a reaction-indifferent inert gas, such as nitrogen or carbon dioxide, and oxygen.

The production method of a pyromellitic anhydride according to the present invention, constituted as above, is instrumental to the attainment of such meritorious effects as enhanced operating rate of a plant and decreased catalyst cost through an improvement in catalyst life and the reduced cost of after-treatments, such as collection and purification, through reductions in byproducts.

BEST MODE FOR CARRYING OUT THE INVENTION

The following examples illustrate the present invention in further detail without defining the scope of the invention.

Catalyst Preparation (Catalyst A)

In 400 ml of deionized water was dissolved 200 g of oxalic acid, and 100 g of ammonium metavanadate was added thereto and evenly dissolved. Then, 3.07 g of ammonium dihydrogen phosphate was added and uniformly admixed. To the mixture thus obtained, 214 g of anatase-form titanium dioxide with a surface area of 20 $m^2/g$, 1.95 g of antimony trioxide, and 17 g of silicon carbide whiskers were added and stirred well to give 600 ml of a homogeneous catalyst component slurry.

An external heating-type rotary furnace was charged with 200 ml of ring-formed silicon carbide carrier having an outer diameter of 7 mm, an inner diameter of 4 mm and a length of 7 mm and the carrier was preheated to 200 to 350° C. This heated carrier was spray-coated with the catalyst component slurry prepared above to support 10 g of the catalyst substance on the carrier while keeping the carrier temperature at 180 to 250° C. The coated carrier was fired in a furnace at 500° C. for 6 hours to give Catalyst A.

(Catalyst B)

In 400 ml of deionized water was dissolved 240 g of oxalic acid, and 100 g of ammonium metavanadate and 15.1 g of ammonium paramolybdate were added and evenly admixed. Then, 3.07 g of ammonium dihydrogen phosphate and 6.53 g of silver nitrate dissolved in a small quantity of deionized water in advance were added and evenly admixed. To this mixture, 214 g of anatase type titanium oxide with a specific surface area of 20 $m^2/g$ and 17 g of silicon carbide whiskers were added and the whole mixture was thoroughly stirred to give 600 ml of a homogeneous slurry of catalyst components. An external-heating type rotary furnace was charged with 200 ml of ring-formed silicon carbide carrier 7 mm in outer diameter and 7 mm long and the carrier was preheated to 200 to 350° C. Then, the carrier was spray-coated with the catalyst component slurry prepared above to support 10 g of the catalyst substance on the carrier while keeping the carrier temperature at 260 to 310° C.

Then, the coated carrier was fired in a furnace at 500° C. for 6 hours to give Catalyst B. The supported catalytic active substance powder was stripped off and recovered and the specific surface area was measured. The result was 18.4 $m^2/g$.

EXAMPLE 1

A tubular reactor having an inside diameter of 25 mm, held in a molten salt bath with an immersed length of 4,000 mm, was packed with Catalyst B over a distance of 900 mm and, on the material gas inlet side thereof, further packed with a 1:1 (by mass) mixture of Catalyst A and SiC rings having an outer diameter of 7 mm, an inner diameter of 4 mm and a length of 7 mm. The reactor was further packed, on top of the above mixture, with the Denston carrier (product of Norton) with an average diameter of 8 mm over a distance of 500 mm.

A starting mixture gas having a durene gas concentration of 30 $g/Nm^3$ as prepared by blending air dehumidified to a moisture content of 0.2 volume % with durene was passed at a space velocity of 4,000 $h^{-1}$ to carry out the reaction. One-hundred (100) liters of the reaction product gas was trapped using an air-cooling type crystallizer and two scrubbing bottles filled with deionized water, and the yield of pyromellitic acid was determined by liquid chromatography and converted to the yield of pyromellitic anhydride. The pyromellitic anhydride yield at 24 hours after the start of reaction was 65.3 mole % and the yield was unchanged even at 2,000 hours. The yield after 4,000 hours of operation was 64.1 mole %.

EXAMPLE 2

Except that the water vapor content of the air used for preparation of the starting mixture gas was adjusted to 2.0 volume %, the reaction and analysis were performed in otherwise the same manner as in Example 1.

The yield of pyromelltic anhydride at 24 hours after the start of reaction was 66.1 mole %. The yield after 1,000 hours of operation was 65.0 mole %, the yield after 2,000 hours was 63.9 mole %, and the yield after 4,000 hours was 61.4 mole %. Thus, the yield was not less than 60 mole % even at 4,000 hours.

COMPARATIVE EXAMPLE 1

Except that the water vapor content of the air used for preparation of the starting mixture gas was adjusted to 5.0 volume %, the reaction and analysis were performed in otherwise the same manner as in Example 1.

The yield of pyromelltic anhydride at 24 hours after the start of reaction was 66.5 mole %. The yield after 1,000 hours of operation was 64.0 mole %, the yield after 2,000 hours was 60.5 mole %, and the yield after 3,000 hours was 54.2 mole %. As the yield had thus fallen below 60 mole %, the operation was terminated.

EXAMPLE 3

The reaction was carried out in the same manner as in Example 1, except that after 100 hours of operation, the water vapor content of the air used for preparation of the starting mixture gas was changed to 2.0 volume % or 5.0 vol. %, and the reaction product gas was analyzed as in Example 1 to investigate the production amount of trimellitic acid under the corresponding conditions.

As a result, the selectivity for trimellitic acid was found to be 2.8 mole % when the water vapor content was 0.2 volume %, 3.5 mole % when it was 2.0 volume %, and 4.5 mole % when it was 5.0 volume %.

(Rate of Decrease in Yield)

When the water vapor concentration was 5.0 volume %, the decrease in yield was 2.5 mole % in the initial 1,000 hours of the reaction but became more pronounced, namely 3.5 mole %, during 1,000–2,000 hours of the reaction, reflecting an acceleration of catalyst aging.

On the other hand, when the water vapor concentration was 2.0 volume % or less, the yield decreased almost linearly during the reaction.

What is claimed is:

1. A production method of a pyromellitic anhydride comprising a step for catalytic gas-phase oxidation of a starting mixture gas consisting of a tetraalkylbenzene and/or a trialkylbenzaldehyde and a molecular oxygen-containing gas in a fixed-bed type reactor having a catalyst bed wherein the production method of a pyromellitic anhydride is carried out under the condition that the moisture content of said starting mixture gas to be introduced into the catalyst bed is not more than 2 volume %.

2. A production method of a pyromellitic anhydride comprising a step for catalytic gas-phase oxidation of a starting mixture gas consisting of a tetraalkylbenzene and/or a trialkylbenzaldehyde and a molecular oxygen-containing gas in a fixed-bed type reactor having a catalyst bed wherein the production method of a pyromellitic anhydride is carried out by dehumidifying the molecular oxygen-containing gas.

* * * * *